United States Patent
Dupinay et al.

(10) Patent No.: US 8,545,870 B2
(45) Date of Patent: Oct. 1, 2013

(54) MEDICINAL TABLE WITH PROLONGED RELEASE OF THE ACTIVE PRINCIPLE

(75) Inventors: Pierre Dupinay, Toutens (FR); Robert Torres, Saint Orens de Gameville (FR); Christine Capon, Ramonville Saint Agne (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 1237 days.

(21) Appl. No.: 10/475,778

(22) PCT Filed: Apr. 25, 2002

(86) PCT No.: PCT/FR02/01421
§ 371 (c)(1),
(2), (4) Date: Jan. 23, 2004

(87) PCT Pub. No.: WO02/085334
PCT Pub. Date: Oct. 31, 2002

(65) Prior Publication Data
US 2006/0171994 A1    Aug. 3, 2006

(30) Foreign Application Priority Data
Apr. 25, 2001  (FR) .................................. 01 05554

(51) Int. Cl.
*A61K 31/465*    (2006.01)
(52) U.S. Cl.
USPC ............. 424/434; 424/435; 424/439; 514/54; 514/343
(58) Field of Classification Search
None
See application file for complete search history.

(56) References Cited

U.S. PATENT DOCUMENTS

| | | | | |
|---|---|---|---|---|
| 4,983,398 A | * | 1/1991 | Gaylord et al. ............... | 424/465 |
| 5,200,194 A | * | 4/1993 | Edgren et al. ................. | 424/473 |
| 5,785,989 A | * | 7/1998 | Stanley et al. ................ | 424/440 |
| 5,942,244 A | * | 8/1999 | Friedman et al. ............. | 424/435 |
| 6,187,342 B1 | * | 2/2001 | Zeidler et al. ................. | 424/486 |
| 6,221,368 B1 | * | 4/2001 | Breitenbach et al. ......... | 424/400 |
| 6,458,400 B1 | * | 10/2002 | Willibald-Ettle et al. ..... | 426/548 |
| 2004/0101543 A1 | * | 5/2004 | Liu et al. ....................... | 424/434 |

FOREIGN PATENT DOCUMENTS

| | | |
|---|---|---|
| EP | 0 839 524 A | 5/1998 |
| EP | 0 839 524 A1 | 5/1998 |
| GB | 1 144 915 A | 3/1969 |
| GB | 1144915 | 3/1969 |
| GB | 2 178 658 A | 2/1987 |
| GB | 2178658 * | 2/1987 |
| WO | 97 42941 A | 11/1997 |
| WO | 97/42941 A2 | 11/1997 |
| WO | WO 9742941 A2 * | 11/1997 |

OTHER PUBLICATIONS

Tilak et al. "Natural Gums and Modified Natural Gums as Sustained-Release Carriers", Drug Development and Industrial Pharmacy, 26(10), 1025-1038 (2000).*
Handbook of Pharmaceutical Excipients, 6th Edition, ed. By R.C. Rowe, P.J. Sheskey, and M.E. Quinn (p. 297) (2009).
Sugar Confectionery Manufacture, ed. by E.B. Jackson (pp. 148-149, 164-165) (1995).
Sugar Confectionery Manufacture, ed. By E.B. Jackson (pp. 8-9, 22-25) (1995).
The Science of Sugar Confectionery, ed. By W.P. Edwards (pp. 140-141) (2001).
Uko-Nne et al., "Dried Molasses as a Direct Compression Matrix for Oral Controlled Release Drug Delivery II: Release Mechanism and Characteristics of Theophylline From a Molasses-HPMC Matrix", Drug Development and Industrial Pharmacy, vol. 15, No. 5 (1989) pp. 719-741.
French Phamacopeia "PELLETS" Xth Edition (Jul. 1987).
Greminger, Jr. et al., Pharmacopee Francaise, Xth Edition, Chapter 3, (Jul. 1987).

* cited by examiner

*Primary Examiner* — Michael G Hartley
*Assistant Examiner* — Nabila Ebrahim
(74) *Attorney, Agent, or Firm* — Birch, Stewart, Kolasch & Birch, LLP.

(57) ABSTRACT

The invention concerns a medicinal tablet to be sucked made with boiled sugar of solid consistency designed to dissolve in the buccal cavity, comprising at least an active principle. The invention is characterized in that it further comprises at least a matrix agent for slowing down the release of the active principle(s) which therefore remain in prolonged contact with the region of the mouth and the pharynx, the dissolving time in the buccal cavity being at least 15 minutes.

9 Claims, No Drawings

MEDICINAL TABLE WITH PROLONGED RELEASE OF THE ACTIVE PRINCIPLE

This application is the national phase under 35 U.S.C. §371 of PCT International Application No. PCT/FR02/01421 which has an International filing date of Apr. 25, 2002, which designated the United States of America.

The invention relates to medicinal pastilles to be sucked, of solid consistency intended to dissolve in the buccal cavity, comprising a matrix agent slowing the release of the active principle(s) in the buccopharyngeal area. The invention likewise relates to a process for production of such a pastille.

Medicinal pastilles to be sucked are already known which are preparations based on sweetening substances, of solid consistency, intended to dissolve in the buccal cavity.

They generally occur in varied forms: spheres, cylinders, squares or any other polygonal form.

These pastilles which are also called cooked sugars are prepared from a syrup of sugary diluent substance raised to boiling, then cooked at a higher temperature, typically from 100° C. to 160° C. To this sugary base are added auxiliary substances such as sweeteners, antioxidants, colorants, flavors, and the active principle(s).

At the end of cooking, the active principle(s) are added to the mass in a mixer as are the auxiliary substances.

The mass thus prepared is kneaded on an appropriate cold surface, then rolled and spun, in order then to be pressed or cut up into pastilles with the desired shape.

These medicinal pastilles to be sucked made of cooked sugar are essentially intended, due to the site where they are dissolved, for the local treatment of the buccal and oropharyngeal area but also for active principles absorbed by the oromucosal route.

Because of this, it is necessary that the active principles chosen for these modes of action are released gradually in order to remain in contact with the buccopharyngeal area for the longest time possible, while avoiding a rapid and massive passage into the digestive tract, which would result in rendering them ineffective at the place of administration or along the chosen route of absorption.

However, the current medicinal cooked sugar pastilles dissolve very rapidly in the mouth, between 5 and 10 minutes maximum, thus releasing too quickly the active principle(s) which they contain and which because of this are immediately swallowed and absorbed at the level of the digestive tract.

The present invention proposes novel medicinal cooked sugar pastilles which allow this disadvantage of the prior art to be compensated for.

With this end in view, the invention relates, according to a first aspect, to a medicinal cooked sugar pastille to be sucked, of solid consistency, intended to dissolve in the buccal cavity, comprising at least one active principle, the pastille further comprising at least one matrix agent allowing the release of the active principle(s) to be slowed, which active principle(s) then remain(s) in prolonged contact with the buccopharyngeal area.

The matrix agent is an agent capable of slowing the dissolution of the cooked sugar in the mouth.

According to one embodiment, the matrix agent further confers on the pastille an increased resistance, lasting even on contact with the saliva, so that the patient cannot bite this pastille and swallow bits of it.

The time of dissolution of the pastille in the buccal cavity is at least 15 minutes, and typically from 25 to 35 minutes, preferably 30 minutes.

The matrix agent is typically chosen from the group formed by noncellulosic polysaccharides, cellulosic derivatives, acrylic acid polymers, fatty substances and polyvinylpyrrolidone, these substances being used alone or as a mixture and representing 1 to 10% by weight of the pastille, typically 1 to 5%.

According to one realization, the matrix agent is chosen from the group formed by: guar gum, carob gum, sodium and potassium alginates, agar-agar, carrageenan, gum arabic, sterculia gum, gum tragacanth.

According to one realization, the matrix agent is chosen from the group formed by hydroxypropylcellulose, hydroxypropylmethylcellulose, hydroxyethylcellulose, ethylcellulose.

According to one realization, the acrylic acid polymer is a carbomer, a polymethacrylate or a copolymer of vinyl acetate.

According to one realization, the fatty substance is chosen from the group formed by waxes, "Gelucire" products, glyceryl behenate, glyceryl palmitostearate.

According to one realization, the matrix agent is polyvinylpyrrolidone.

The pastille further comprises a major sugary exipient, or diluent, chosen from sucrose, fructose, lactose, sorbitol, mannitol, lactitol, glucose, maltitol, isomalt, polydextrose and maltodextrins, used alone or as a mixture, representing 80 to 99% by weight of the pastille.

According to one realization, the pastille further comprises at least one auxiliary substance chosen from sweeteners, antioxidants, colorants and flavors.

According to a preferred realization, the invention relates to a pastille comprising nicotine as active principle.

According to a preferred realization, the pastille comprises isomalt, methocel (hydroxypropyl-cellulose), nicotine and a sweetening agent with strong sweetening power, especially aspartame.

According to another aspect, the invention relates to a process for production of a medicinal pastille described above, comprising successively:
  a step of boiling a syrup of sugary diluent substance;
  a step of cooking at a higher temperature, of the order of 100° C. to 160° C.;
  a step of mixing with incorporation of the active principle(s) and of the auxiliary substance(s);
  a step of production of the cooked sugar pastille;
    the matrix agent being incorporated either in the course of the boiling step, or in the course of the cooking step, or during mixing.

Other aspects and advantages of the invention will appear during the detailed description which follows. The matrix agent allows the dissolution of the cooked sugar in the mouth to be slowed and, by the same token, the release of the active principle(s) at the site of action to be slowed.

Moreover, unexpectedly, contrary to what would have been thought, the matrix agent confers on the cooked sugar pastille a great resistance, even lasting in contact with the saliva, superior to that customarily obtained with this type of preparation, so that it becomes impossible for the patient to bite this pastille and to swallow bits of it.

This complementary phenomenon is particularly favorable to the prolonged effect sought at the site of action, since the patient finds himself/herself having to allow the pastille to melt in the mouth until it is completely dissolved.

The time of dissolution in the buccal cavity obtained with this novel form of cooked sugar pastilles can attain 30 minutes. This time can be modulated as a function of the choice of the sweetening agent(s) and of the matrix agent(s).

These novel cooked sugar pastilles can have any of the customary geometric shapes already mentioned beforehand.

They are composed in a high proportion of a sugary diluent substance or excipient forming the basis of the preparation, which can be: sucrose, fructose, lactose, sorbitol, mannitol, lactitol, glucose, maltitol, isomalt, polydextrose, maltodextrins, etc.

Among the noncellulosic polysaccharides which can be used are especially to be mentioned: guar gum, carob gum, sodium and potassium alginates, agar-agar, carrageenan, gum arabic, sterculia gum, gum tragacanth, xanthan gum, gum tragacanth, gum karaya.

Among the utilizable cellulose derivatives, the following derivatives are to be preferred: hydroxypropylcellulose, hydroxypropylmethylcellulose, hydroxyethylcellulose, ethylcellulose. The hydroxyethylcelluloses are described, for example, in "*Handbook of water-soluble gums and resins*", ed. R. L. Davidson, pub. McGraw-Hill (1980). It may also be especially possible to use the derivatives: carboxymethylcellulose (CMC), methylcellulose (MC), ethylhydroxyethylcellulose (EHEC), hydroxyethylmethylcellulose (HEMC), modified hydroxyethylcellulose (HMHEC), modified ethylhydroxyethylcellulose (HMEHEC), carboxymethylhydroxyethylcellulose (CMHEC).

The substances forming the matrix agent can be used alone or as a mixture. Their choice and their concentrations will depend on the sweetening substance(s) used, on the active principle(s) selected and on their activity, on the time of dissolution in the mouth and on the texture of the cooked sugar desired.

The major sugary excipient, or diluent, is chosen from the sugary substances mentioned above used alone or in combination, there too as above, as a function of the desired result.

The auxiliary substances are those customarily employed: sweeteners, antioxidants, colorants, flavorings, etc.

The production process according to the invention comprises four steps: a boiling step, a cooking step, a mixing step, a step of production of the cooked sugar pastilles.

The production step complies with current pharmaceutical requirements. The active principle can be, for example: nicotine, chlorhexidine digluconate, tetracaine, cetylpiridinium, plant extract.

The matrix agent can be incorporated either in the course of the boiling step, or in the course of the cooking step, or during mixing.

The choice of the step for incorporating the matrix agent will depend on the desired final characteristics of the cooked sugar pastilles.

The pastilles thus obtained are very different from other pharmaceutical forms, such as tablets capable of containing some of the noncellulosic polysaccharides and cellulosic derivatives mentioned above.

In fact, the pastille pharmaceutical form is quite specific, having been the subject of a monograph in the French Pharmacopeia Xth Edition (July 1987). The pastilles are saccharoids of solid consistency intended to disintegrate slowly in the buccal cavity. They are present especially in a hemispherical form and generally weigh between 1 g and 3 g. They are generally composed of a high proportion of sucrose, of a binding substance such as gum arabic or gum tragacanth, of one or more active principles and optionally of auxiliary substances (colorants, flavorings, etc.). The pastilles are prepared by first producing a paste with one part of sucrose. This paste is heated to gentle boiling. The remainder of the sucrose, the active principle(s) and the auxiliary substances are then added. After homogenization, the mass thus prepared is made to fall drop by drop onto a cold plate or it is injected into an appropriate mold.

Thus the pastille differs clearly from tablets:

by its mode of use, by its composition, and especially the excipients used (sucrose, isomalt, maltitol, fructose, glucose) and their high concentration of the order of 80 to 99% of the formula, by its specific mode of preparation, totally different from tablets, and necessitating a specific apparatus:

cooking of the mixture under vacuum from which the term <<cooked sugar>> arises mixing and cooling of the paste obtained on a cold table equipped with a kneader extrusion of the mass pressing on a press totally different from a tableter In particular, the percentage of matrix agent in the pastilles is low, of the order of 1 to 10%, preferably of 1 to 5%.

Some examples of pastilles according to the invention are presented below.

EXAMPLE 1

| | |
|---|---|
| Chlorhexidine digluconate | 3.000 mg |
| Tetracaine hydrochloride | 0.200 mg |
| Ascorbic acid | 52.500 mg |
| Hydroxypropylmethylcellulose | 100.000 mg |
| Isomalt | 2317.1875 mg |
| Ammonium glycyrrhizinate | 5.000 mg |
| Aspartame | 1.000 mg |
| Flavor | QS |
| Water | QS |

EXAMPLE 2

| | |
|---|---|
| Chlorhexidine digluconate | 3.000 mg |
| Ascorbic acid | 52.500 mg |
| Hydroxypropylmethylcellulose | 50.000 mg |
| Maltitol | 2425.000 mg |
| Erythrosin | 0.250 mg |
| Flavors | QS |
| Water | QS |

EXAMPLE 3

| | |
|---|---|
| Cetylpyridinium | 2.500 mg |
| Benzocaine | 2.000 mg |
| Vitamin C | 52.500 mg |
| Hydroxypropylmethylcellulose | 100.000 mg |
| Isomalt | 2425.000 mg |
| Flavors | QS |
| Water | QS |

EXAMPLE 4

| | |
|---|---|
| Extract of erysimum | 15.000 mg |
| Carrageenate | 100.000 mg |
| Sucrose | 1471.250 mg |
| Glucose | 1000.000 mg |
| Ammonium glycyrrhizinate | 1.000 mg |
| Flavor | QS |
| Water | QS |

EXAMPLE 5

| | |
|---|---|
| Nicotine | 1.000 or 2.000 mg |
| Hydroxypropylmethylcellulose | 100.000 mg |
| Cyclodextrin | 50.000 mg |
| Isomalt | 2306.083 mg |
| Aspartame | 0.750 mg |
| Flavor | QS |
| Water | QS |

EXAMPLE 6

| | |
|---|---|
| Amylein hydrochloride | 2.000 mg |
| Cetylpyridinium hydrochloride | 1.000 mg |
| Polyvinylpyrrolidone | 100.000 mg |
| Sucrose | 1577.000 mg |
| Glucose | 820.000 mg |
| Flavor | QS |
| Colorant | QS |
| Water | QS |

EXAMPLE 7

| | |
|---|---|
| Dextromethorphan hydrobromide | 20.000 mg |
| Citric acid | 37.000 mg |
| Polymethacrylate | 50.000 mg |
| Sucrose | 1256.000 mg |
| Glucose | 1111.000 mg |
| Flavor | QS |
| Water | QS |

EXAMPLE 8

Unit Formula

| Raw Materials | Quantity |
|---|---|
| Isomalt type M | 2350.10 mg |
| Methocel K 15 M | 100.00 |
| Nicotine Polacrilex titrated 18% | 11.835 |
| Aspartame | 0.750 |
| Acesulfam K | 1.250 |
| Peppermint flavor 13-571-016 | 16.00 |
| Peppermint flavor 13-627-517 | 20.00 |
| Total | 2500 mg |

EXAMPLE 9

Unit Formula

| Raw Materials | Quantity |
|---|---|
| Isomalt type M | 2338.76 mg |
| Methocel K 15 M | 100.00 |
| Nicotine Polacrilex titrated 18% | 11.835 |
| Aspartame | 0.900 |
| Acesulfam K | 1.500 |
| Peppermint flavor 13-571-016 | 8.00 |
| Dry extract of deglycyrrhizinated liquorice | 37.50 |
| Ammonium glycyrrhizinate | 1.500 |
| Total | 2500 mg |

Thus, the pastille of examples 8 and 9 comprises 2.1303 g of nicotine.

The production of these pastilles is carried out hot. The matrix agent is incorporated into the sweetening base at a temperature of the order of 70 to 95° C. (boiling step), preferably at 90° C. The whole is then heated to approximately 130° C. at the time of cooking. The nicotine is then added (mixing step) to the mass at a temperature of the order of 110 to 130° C., preferably 120° C.

The nicotine Polacrilex is a complex of nicotine $C_{10}H_{14}N_2$ with an ion exchange resin (carboxylate cationic resin); this complex has the formula: $C_{10}H_{14}N_2 (C_{18}H_{22}O_4)_n$.

The invention claimed is:

1. A medicinal cooked sugar pastille to be sucked, of solid consistency, intended to dissolve in the buccal cavity, comprising nicotine as active principle, which further comprises an excipient, consisting of isomalt, representing 80 to 99% by weight of the pastille and a matrix agent consisting of hydroxypropylmethylcellulose, representing 1 to 10% by weight of the pastille allowing the release of the active principle to be slowed, which active principle is then in contact with, and absorbed by the oromucosal route, the time of dissolution in the buccal cavity being at least 15 minutes; wherein the medicinal cooked sugar pastille is made by
   boiling a syrup of the isomalt;
   cooking at a higher temperature, of the order of 100° C. to 160° C.;
   mixing with incorporation of the nicotine; and
   producing the pastille;
   the matrix agent being incorporated during boiling, cooking step, or mixing.

2. The pastille as claimed in claim 1, wherein the at least one matrix agent represents 1 to 5% by weight of the pastille.

3. The pastille as claimed in claim 1, wherein the matrix agent is an agent capable of slowing the dissolution of the cooked sugar in the mouth.

4. The pastille as claimed in claim 1, wherein the matrix agent further confers on the pastille an increased resistance, lasting even on contact with the saliva, so that the patient cannot bite this pastille and swallow bits of it.

5. The pastille as claimed in claim 1, wherein the time of dissolution of the pastille in the buccal cavity is from 25 to 35 minutes.

6. The pastille as claimed in claim 1, which further comprises at least one auxiliary substance chosen from sweeteners, antioxidants, colorants and flavors.

7. The pastille as claimed in claim 1, which further comprises hydroxypropylcellulose and aspartame.

8. A process for production of a medicinal pastille as claimed in claim 1, which comprises successively:
   boiling a syrup of an excipient consisting of isomalt;
   cooking at a higher temperature, of the order of 100° C. to 160° C.;
   mixing with incorporation of the active principle and of the auxiliary substance(s); and
   producing the pastille;

the matrix agent being incorporated during boiling, cooking step, or mixing.

9. The pastille as claimed in claim 1, wherein the time of dissolution of the pastille in the buccal cavity is about 30 minutes.

* * * * *